United States Patent
Mueller et al.

(10) Patent No.: US 6,345,203 B1
(45) Date of Patent: Feb. 5, 2002

(54) SYSTEM AND METHOD FOR POWERING, CONTROLLING, AND COMMUNICATING WITH MULTIPLE INDUCTIVELY-POWERED DEVICES

(75) Inventors: Jeffrey S. Mueller, Raleigh; H. Troy Nagle, Durham; Ronald S. Gyurcsik, Cary; Arthur W. Kelley, Raleigh, all of NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 09/436,674

(22) Filed: Nov. 9, 1999

Related U.S. Application Data

(62) Division of application No. 09/094,260, filed on Jun. 9, 1998, now Pat. No. 6,047,214.

(51) Int. Cl.[7] ............................................. H02J 17/00
(52) U.S. Cl. ........................ 607/60; 607/61; 332/149; 340/870.18
(58) Field of Search ............................. 607/60, 61, 2, 607/32, 33; 128/903; 332/149; 340/870.01, 870.18, 870.32, 573.1, 870.11, 825.69, 10.34

(56) References Cited

U.S. PATENT DOCUMENTS

| | | | | |
|---|---|---|---|---|
| 4,368,352 A | * | 1/1983 | Davis | 178/19 |
| 4,561,443 A | * | 12/1985 | Hogrefe et al. | 128/419 |
| 5,701,121 A | * | 12/1997 | Murdoch | 340/825 |
| 5,999,857 A | * | 12/1999 | Wejand et al. | 607/60 |
| 6,047,214 A | * | 4/2000 | Mueller et al. | 607/16 |

OTHER PUBLICATIONS

Ko et al., "RF–Powered Cage System for Implant Biotelemetry" vol. BME–27, No. 8, IEEE Transactions on Biomedical Engineering, pp. 460–467 (Aug., 1980).

Schuder et al., "Energy Transport Into the Closed Chest From a Set of Very–Large Mutually Orthogonal Coils", vol. 82, No. 64, Communications and Electronics, pp. 132–137 (Jan., 1963).

Singh et al., "A Mercuric Iodide Detector Unit Implantable and Externally Powered for Use in Radionuclide Tracer Studies in Small Animals", vol. 8, Biotelemetry Patient Monitoring, pp. 204–212 (1981).

* cited by examiner

Primary Examiner—Kennedy Schaetzle
(74) Attorney, Agent, or Firm—Jenkins & Wilson, P.A.

(57) ABSTRACT

Magnetic Vector Steering (MVS) and Half-Cycle Amplitude Modulation (HCAM) are novel techniques which enhance the powering and control of multiple arbitrarily oriented implant devices. Together, these techniques enable arbitrarily oriented implants to receive power and command, programming, and control information in an efficient manner that preserves battery life and transmission time while reducing overall implant device bulk. By steering the aggregate magnetic field from a near-orthogonal set of AC-energized coils, selected implants can be powered or communicated with at desired times. Communication with individual implants can also be enhanced through half-cycle amplitude modulation —a technique that allows bit rates up to twice the energizing frequency. Unlike prior art systems, power and data transfer can be realized over the same frequency channel.

2 Claims, 8 Drawing Sheets

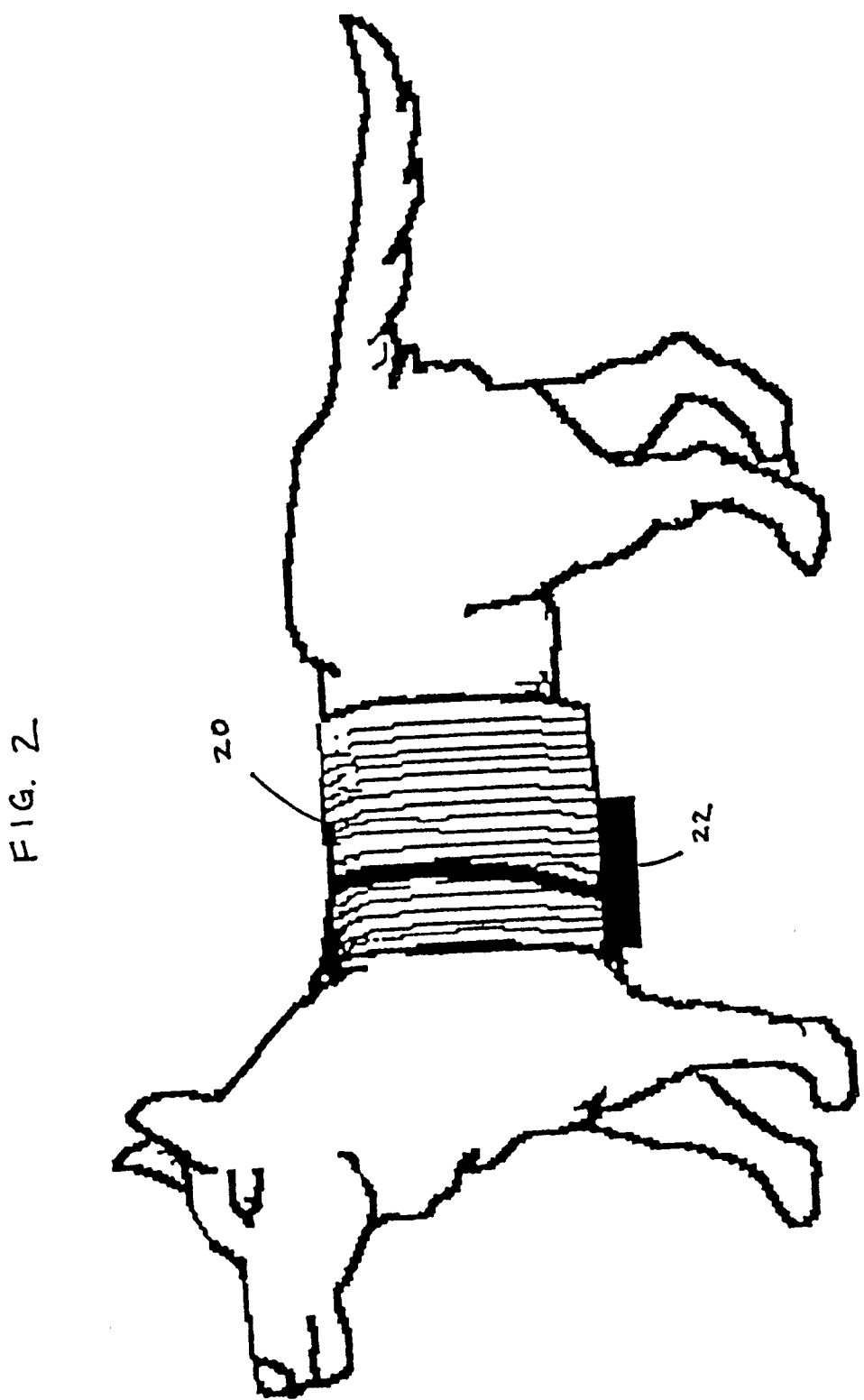

SYSTEM AND METHOD FOR POWERING, CONTROLLING, AND COMMUNICATING WITH MULTIPLE INDUCTIVELY-POWERED DEVICES

This application is a division of U.S. patent application Ser. No. 09/094,260, filed Jun. 9, 1998 now U.S. Pat. No. 6,047,214, disclosure of which is incorporated by reference herein in its entirety.

TECHNICAL FIELD

The present invention relates to techniques for enhancing the powering of and wireless data collection from arbitrarily oriented high-bandwidth remote sensor devices such as inductively powered implant devices.

BACKGROUND ART

For the past three decades, biotelemetry has assisted many researchers and clinicians in obtaining physiological information from both patients and animals. With the development of new electronic, communication, battery, and material technologies, the capabilities of biotelemetry systems have expanded, bringing increased performance in the form of longer implantation times, greater channel counts, smaller sizes, and more robust communication.

For a majority of medical applications using biotelemetry implants, it has sufficed to monitor only a few channels of slowly varying DC levels such as pressure, temperature, ion concentration, etc. or small bandwidth signals with bandwidths typically ranging from 100 Hz to 5 kHz per channel such as EKG, EEG, EMG, etc. To date, however, biotelemetry systems have been unable to provide the throughput necessary for certain applications, such as cardiac mapping or high-bandwidth multichannel neural recording in which channel rates in excess of 1 Mbits/sec are often required, thus mandating large amounts of energy to power the implant. For long term studies, the energy requirement becomes even more prohibitive.

Researchers are currently searching for data collection systems that can maximize usage of developing, high-bandwidth sensor systems. Such sensor systems include flexible plastic substrate-based biosensor arrays for biopotential recording, and silicon-based micro-electrode arrays for neural recording.

Also of interest is the ability to collect physiological information from a variety of locations within a subject. This requires a network of sensors placed throughout a region under study. In cardiac mapping, for example, several electropotential arrays may be required at different ischemic or infarcted areas of a heart in order to simultaneously monitor electrical activity during a cardiac event. A desirable implementation for this network has each sensor as a separate telemeter, thereby eliminating the need to interconnect wires among the sensors. The elimination of these wires significantly reduces overall implant bulk and complexity while facilitating implantation.

A fundamental difficulty in developing a high-bandwidth biotelemetry system pertains to implant power consumption. In contrast to low-bandwidth systems, a high-bandwidth system must transmit many more pulses in a given time-period, thus depleting the power source much faster. In addition, the electronics required to sample, process, and encode the sensor data will also draw more energy as the aggregate bandwidth increases. The increased power demands require the use of larger implant batteries or alternative power sources. A popular widely known alternative to relying exclusively on batteries to power an implant is Inductive Power Transfer (IPT).

Inductive Power Transfer uses an AC-energized coil to create a magnetic field that couples with a receiving coil of an inductively powered device. The induced signal appearing at the output of the inductively powered device coil is then rectified and filtered to create a relatively constant DC power source. The "loosely-coupled transformer" link provides a means of eliminating and/or recharging inductively coupled biomedical implant batteries or capacitors. This technique has been used not only for biotelemetry devices, but also for artificial hearts, ventricular assist devices, various forms of neural stimulators, and battery recharging.

What is needed is a system which can accurately target arbitrarily oriented inductively powered devices in order to provide power to, and communicate at high data rates with, the arbitrarily oriented inductively powered devices.

DISCLOSURE OF THE INVENTION

The present invention pertains to a system capable of high-bandwidth communication and omnidirectional power transfer to a network of arbitrarily positioned inductively powered devices. Magnetic Vector Steering (MVS) and Half-Cycle Amplitude Modulation (HCAM) are two novel techniques which enhance the powering and control of multiple inductively powered devices. Together, these techniques enable arbitrarily oriented inductively powered devices to receive power and command/programming/control information in an efficient manner that preserves battery life and transmission time. By directing the aggregate magnetic field, using magnetic vector steering, from a near-orthogonal set of AC-energizing coils, selected inductively powered devices can be powered and/or communicated with at desired times. Communication with individual inductively powered devices can also be enhanced through half-cycle amplitude modulation—a technique that allows bit rate transfers up to twice the energizing frequency. The present invention combines power and data transmission circuitry more effectively than the prior art while also significantly reducing the hardware required of an inductively powered device such as a biomedical implant thereby reducing overall implant bulk.

It is an object of the present invention to provide a system for remotely powering one or more inductively powered devices such that the overall bulk of such devices is significantly reduced.

It is a further object of the present invention to provide a data communication system which can modulate a power carrier, communicating with one or more inductively powered devices, with a serial data stream at upto twice the cycle rate of the power carrier.

It is a still further object of the invention to allow the use of a single frequency channel for both power and data transfer to arbitrarily oriented inductively powered devices.

Some of the objects of the invention having been stated, other objects will become apparent as the description proceeds, when taken in connection with the accompanying drawings described as follows:

BRIEF DESCRIPTION OF THE DRAWINGS

FIG. 2 illustrates an energizing coil assembly integrated into a harness as worn by, for instance, a dog;

DETAILED DESCRIPTION OF THE INVENTION

Figure 1A:
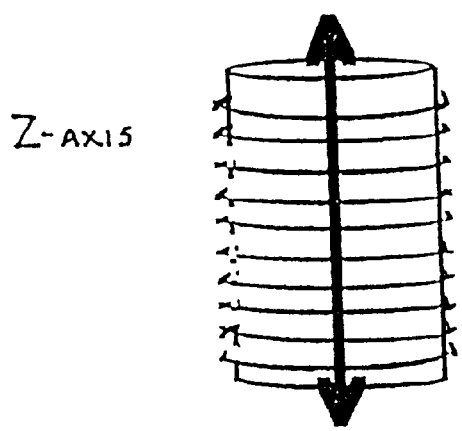
FIG. 1A illustrates a cylindrical "long solenoid" magnetic coil as one example of a magnetic coil which provides control of a magnetic vector along the z-axis.

The present invention is described more fully hereinafter with reference to the aforementioned drawings, in which preferred embodiments of the invention are shown. This invention may, however, be embodied in many different forms and should not be construed as limited to the embodiments set forth herein.

Although inductive links such as Inductive Power Transfer (IPT) have been used extensively for both powering of and communication with inductively powered devices, there are several limitations with respect to their use. When multiple and/or arbitrarily positioned inductively powered devices are energized by an external coil(s), a burdensome diversity scheme is required to ensure that a sufficient degree of magnetic coupling exists between the external "energizing" coil(s) and the inductively powered device coil(s).

Two approaches have typically been used. One common approach is to use multiple energizing coils excited at different frequencies such that the collection of energizing coils possess near orthogonal magnetic vector components. Another approach is to use a single energizing coil and multiple, orthogonally-oriented, receiving coils.

The chief drawback to the former technique is that the multiple energizing coils are unsynchronized in operation (i.e. driven at slightly different frequencies), resulting in a magnetic field spanning in all directions, thus wasting source energy. The chief drawback to the latter technique is that an increase in implant (i.e., inductively powered device) volume, and complexity must be afforded due to having multiple receiving coils for each device.

The Magnetic Vector Steering (MVS) scheme of the present invention uses an energizing coil assembly that supplies power to specific inductively powered devices (stimulators, telemeters, etc.) through the superposition of magnetic fields from separate energizing coils. Unlike previous systems, however, power transfer is not restricted by the orientation of the inductively powered devices, with only a single power-receiving coil. Moreover, the energizing coils are synchronized and therefore operable over the same frequency channel eliminating the problem of having the energizing coil magnetic field propagate inefficiently in all directions. An assembly of external coils is arranged to strategically maneuver a net magnetic field toward a specific inductively powered device within a set of such devices. This technique conserves source energy, since the magnetic vector is kept from wandering in directions where energy transfer to the inductively powered devices is minimal.

In one exemplary embodiment, the external coil assembly was chosen to conform to a cylinder integrated into a harness to be worn by an animal. The coils that comprise the assembly for this embodiment include a "long solenoid" and two pairs of "saddle coils". Each of these coils has been shown to exhibit magnetic fields highly uniform both in magnitude and direction throughout the majority of their respective interiors. The long solenoid coil illustrated in FIG. 1A provides control of the magnetic vector along the z-axis of the cylinder, while the saddle coils illustrated in FIGS. 1B and 1C provide control in the x-axis and y-axis of the cylinder, respectively.

Figure 1B:
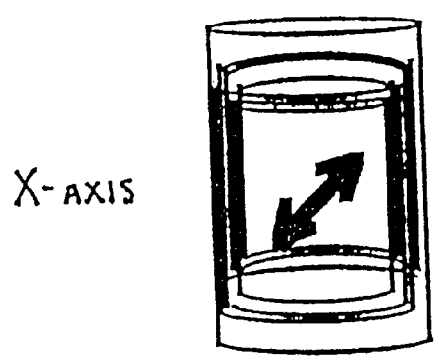
FIG. 1B illustrates a cylindrical "saddle coil pair" as one example of a magnetic coil which provides control of a magnetic vector along the x-axis.
Figure 1C:
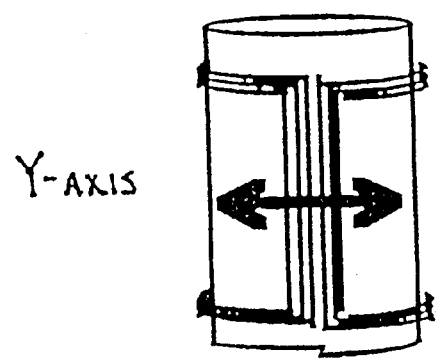
FIG. 1C illustrates a cylindrical "saddle coil pair" as one example of a magnetic coil which provides control of a magnetic vector along the y-axis.

FIG. 2 illustrates a harness 20, as worn by a dog, which includes the coils of FIGS. 1A–C. The harness 20 is powered, in this instance, by a battery pack source 22. Other coil types and harnesses, however, may be used in conjunction with the present invention. That is, the combination of two saddle coils and a long solenoid coil described above need not be the only energizing coil implementation. Any coil assembly that can direct a magnetic vector along the x-axis, y-axis, and z-axis will suffice.

Figure 3:
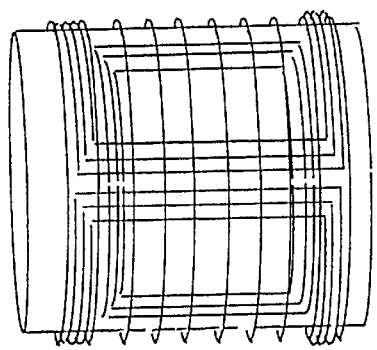
FIG. 3 illustrates one embodiment of an energizing coil assembly.

FIG. 3 illustrates a coil assembly which can be integrated with a harness system like the one illustrated in FIG. 2. The coil assembly is a single unit which includes a plurality of separate coils such that the collection of coils is capable of radiating a magnetic field in the x-, y-, and z-axes. By varying the energy supplied to each coil, the magnitude and direction of the resulting magnetic field vector can be controlled. Using this technique together with knowledge of the orientation of a set of inductively powered devices, the present invention is capable of targeting a specific device to provide power to and moving to each device in the set in a prescribed or adaptive pattern.

Figure 4:
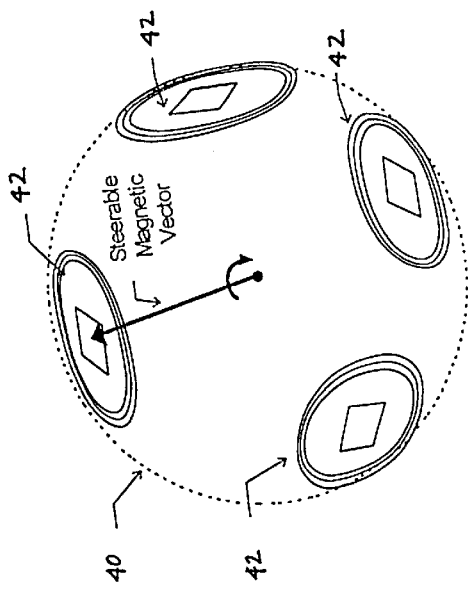
FIG. 4 illustrates a region, such as, for instance, a heart having multiple implant sensor devices about its periphery.

FIG. 4 illustrates a sphere 40 which could represent, for instance, the heart of an animal. About the sphere 40 are a plurality of arbitrarily oriented inductively powered coil devices 42. These devices 42 can take the form of biomedical implants which monitor various characteristics of the animal's heart. Upon sufficient coupling with an outside source such as the coil assembly of FIG. 3, these implants will be able to power themselves and even transmit data back to an external receiving device (not shown) for diagnostic processing. The system can be programmed with the locations of each implant so the coil assembly can be energized at specific levels such that each implant device is coupled with the energizing coil assembly. The program can be "adaptive", monitoring the energy status of inductively powered devices and scheduling time-slots or dwell times for energy transfer.

Figure 6:
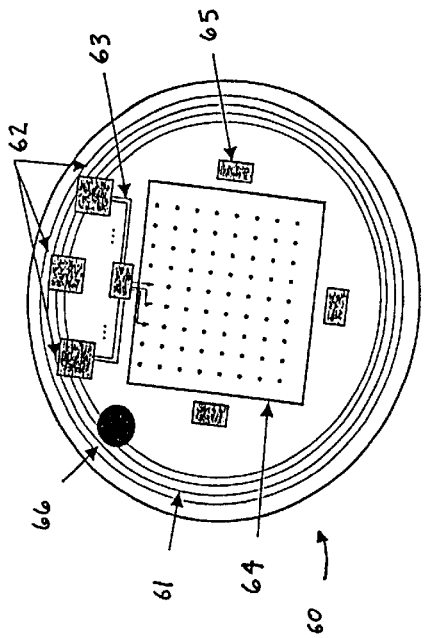
FIG. 6 illustrates a second type of inductively powered biomedical implant device geometry suitable for use with the present invention.
Figure 5:
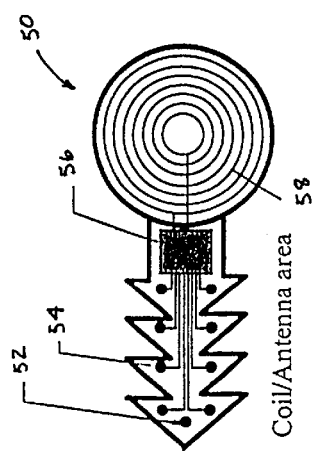
FIG. 5 illustrates one type of inductively powered biomedical implant device geometry suitable for use with the present invention.

FIGS. 5 and 6 illustrate two examples of inductively powered devices suitable for biomedical implantation applications. Referring now to FIG. 5, the implantable device 50 appears key-like in shape and has a reference electrode 52 positioned near the tip of the device 50. A network of sensor sites 54 span the tip and "key" area and are electrically connected to an integrated circuit chip 56. Integrated circuit chip 56 in turn is connected to a coil/antenna 58 which serves to couple with an external energizing coil (not shown) in order to receive power and also to send data out to a receiving device (not shown). Referring now to FIG. 6, implantable device 60 is circular in shape having its coil 61 wrapped about the outer periphery of the circular area. Telemetry and power conditioning circuitry 62 connects via metal interconnection traces 63, to coil 61 and signal processing electronics 65. Lastly, a power supply filtering capacitor or a small battery 66 is shown coupled to the coil 61. The power supply filtering capacitor or a small battery 66 can charge itself and power the implant for a period of time should the external energizing coil (not shown) be temporarily de-activated or de-coupled.

Figure 7:
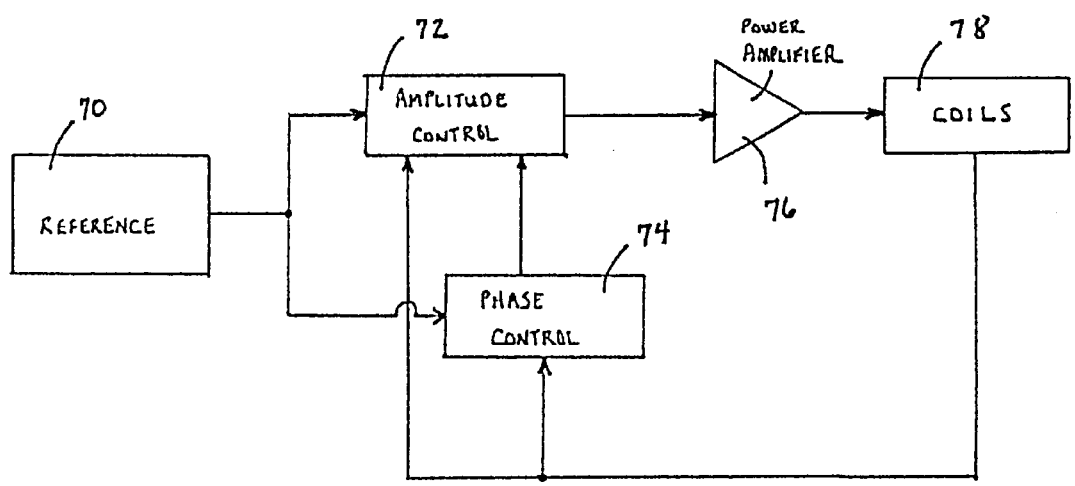
FIG. 7 illustrates a simplified block diagram of the magnetic vector steering (MVS) system according to the present invention.

A simplified block diagram of the magnetic vector steering system is illustrated in FIG. 7. A reference power source 70 is used to provide a stable clock source that generates a power carrier frequency signal. The signal from the reference power source 70 is fed to both amplitude control 72 and phase control 74 blocks. The output of the amplitude control block 72 is passed to a power amplifier 76 in order to provide sufficient drive capabilities for an energizing coil 78. The energizing coil 78 then sends feedback to both the amplitude 72 and phase 74 control blocks in order to stabilize the system. A similar configuration is used for each of the coils that comprise the coil assembly.

For the present magnetic vector steering (MVS) system, amplitude control ranges over a factor of ten (10), while phase ranges from nearly −180° to 180°. Phase shift results while changing the pulse width of the driving waveforms.

Figure 8:
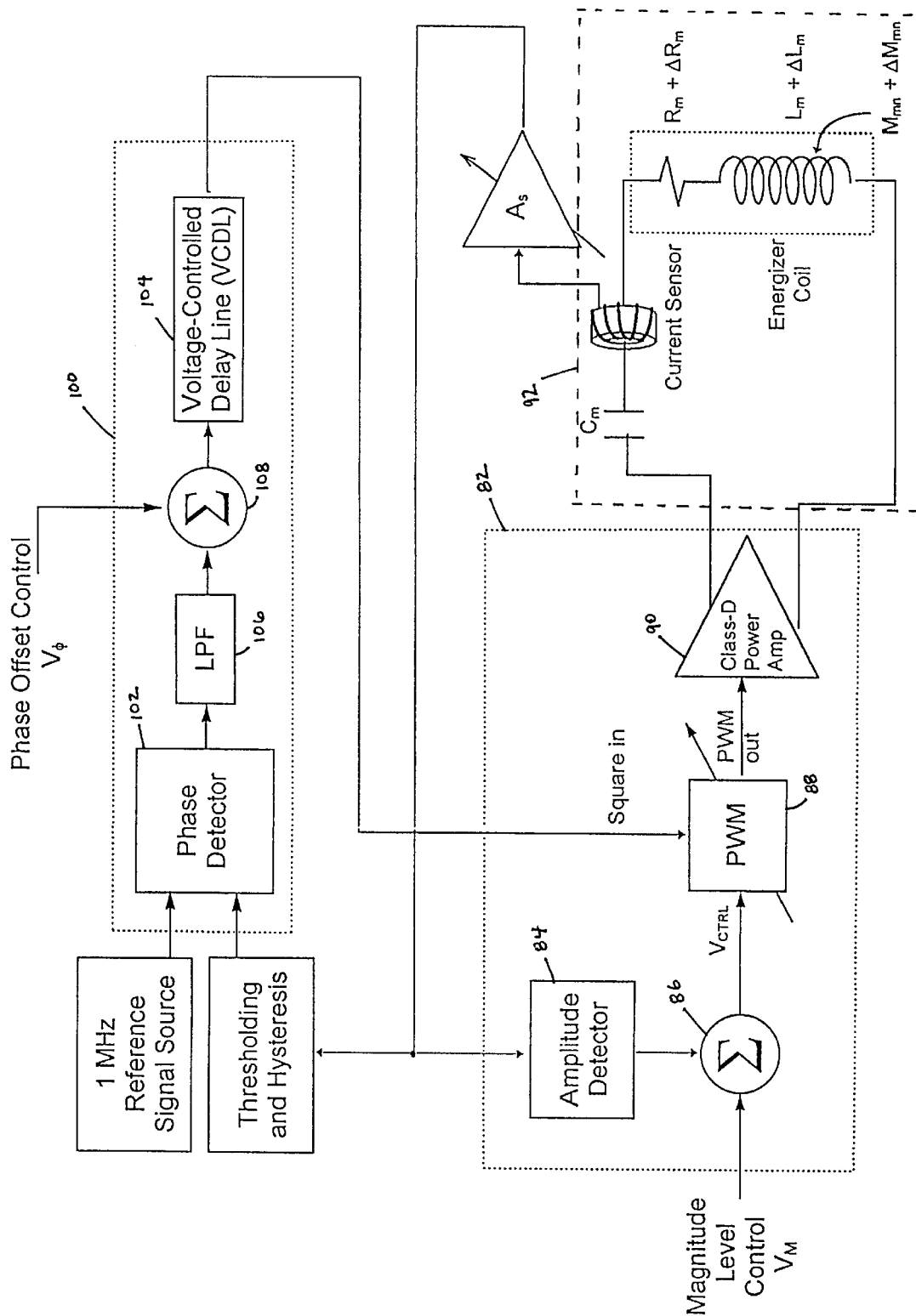
FIG. 8 illustrates a more detailed block diagram of the magnetic vector steering (MVS) system according to the present invention.

Referring now to FIG. 8, popular compensation techniques such as those described below are either undesirable or impractical for the present invention. Altering the driver reference frequency will not accommodate variations in resonant frequencies of all coil circuits, both external and implanted. Tuning diodes (varactors) are undesirable, since they are highly non-linear over large voltage swings and their biasing is impractical. Likewise, transductor-based compensation is also undesirable on account of similar non-linearity problems as well as increased weight, size, and power consumption (a strong DC current is required to alter a transductors inductance).

The present invention, however, stabilizes coil currents in both magnitude and phase through the use of two feedback loops. One feedback path acts to compensate for magnitude variations through automatic gain control. The other feedback path nulls-out phase errors by using a delay-locked loop (DLL).

Automatic gain control 82 is achieved by detecting the amplitude 84 of a particular energizing coil current and comparing 86 it to a pre-selected value, $V_m$. The resulting error term modulates a pulse width of a pulse-width modulator 88 (PWM), thereby changing the amplitude of the first harmonic at its output. The pulse-width modulator drives a Class-D power amplifier 90, which in turn drives a resonant coil network 92. The magnitude of the output resonant circuit is related to the amount of first harmonic in the PWM power signal. Hence, changes in the amplitude error signal spur counter changes in the amplitude of the resonant coil network 92.

With regard to the phase compensation circuit 100, a delayed locked loop (DLL) corrects for phase shifts by comparing the phase of the reference frequency with that of the coil current. Phase error is used to drive a voltage-controlled delay line (VCDL) 104, thus varying the phase of the PWM input signal, the power driver circuit, and hence, the resonant coil network phase. In this way, changes in the phase error signal bring about counter changes in the resonant coil network phase.

As shown in FIG. 8, this dual-feedback system requires that both feedback mechanisms operate in conjunction with one another without making the system unstable. This is because the gain compensation block 82 uses the output signal from the phase correction block 100 as its input reference frequency.

The delay locked-loop portion of the phase control block 100 is a familiar block seen in other delay locked-loop applications. It comprises a phase detector 102, a low-pass filter 106, and a voltage-controlled delay line (VCDL) 104. A summation node 108 has also been added in order to allow for user adjustment of the phase.

The phase detector 102 most suitable is an XOR-type detector, augmented with lead/lag detection. This type of detector can indicate phase differences from −pi to +pi radians. Because the output of this detector is comprised of digital logic pulses of varying width, as well as a lead/lag bit, it must be used in conjunction with a low-pass filter 106 that removes the AC component of the XOR output signal. The lead/lag bit controls the polarity of the gain. Under real circumstances, however, a small ripple penetrates the low-pass filter 106, thus contributing to unmodeled error in the system.

The output of the phase detector 102 and low-pass filter 106 is fed to a summation node 108, where a phase offset component can be added. Such an input is desirable for setting the bias level of the voltage control delay line (VCDL) 104 that follows, so that VCDL operation can occur at its center or most linear region of operation. The voltage-controlled delay line (VCDL) 104 delays the reference signal by a phase that is proportional to an input control voltage.

The Magnetic Vector Steering (MVS) system described above is capable of powering one or more inductively powered implant devices such as, for instance, certain biomedical implants using a fixed or adaptive scheduling algorithm. If the total energy requirements of a set of implant devices can be met by an energizing coil assembly, then a standard round-robin scheduling method can be employed to inductively power each implant device with the energizing coil assembly dwell time on each implant device being proportional to its energy requirements. Another standard method would be to create fixed energizing coil assembly dwell time segments, and to allocate a number of these specific segments to each implant device.

Adaptive scheduling may also be used to power the implant devices in cases when the energizing coil assembly can not meet the power needs of all of the implant devices. If each implant device can communicate its stored energy status to the energizing coil assembly, then the implant devices with the highest priority can be scheduled for dwell time on an as needed basis. Such an adaptive scheduling system would be highly effective in applications for which the energy requirements for individual implant devices are time-varying.

Another limitation of prior art inductively powered link systems is the limited bandwidth of the energizing coils. Ordinarily, medium-Q to high-Q coils are resonated to maximize coupling efficiency and remove undesired harmonics. The Q of a coil represents the resonant peak of circuit response. Narrowband coils, however, restrict the communication rate of the link, due to the increase in response time with coil Q. For example, it can be easily shown that for the magnitude of an energizing coil current to settle within 5% of its final value (indicative of a complete bit transition in AM), it would take a number of cycles of the power carrier roughly equal to the Q of the coil. Hence for a nominal energizing coil Q of 50, fifty power carrier cycles would be required to register a bit transition. This response time can greatly reduce system throughput if inductively powered devices are required to transmit information upon command of the external energizing coil assembly.

The present invention, however, allows bit transitions to occur up to every half-cycle of the power carrier using a technique known as Half-Cycle Amplitude Modulation (HCAM). This greatly decreases the time required to send command information to, or otherwise communicate with, inductively powered devices.

The principle behind half-cycle amplitude modulation is that current can be made to circulate within all or a fractional number of turns of an energizing coil or coils, thus amplitude modulating the magnetic field. However, when a portion of the coil is instantaneously removed or switched out from the RLC circuit, the circuit dynamics are changed. The removal of a coil section decreases the inductance of the circuit, which in turn shifts the band-pass filter spectra toward infinity. As a result, the driving frequency no longer coincides with the RLC resonant frequency, and changes in both current amplitude and phase manifest. These changes must also "settle" according to the band-pass characteristics of the RLC network, thus requiring a settling time.

If, however, an inductor with equivalent impedance (both real and imaginary) to the removed section is substituted or switched in for the removed section, the circuit dynamics will remain the same. The key to the substitution (or switching) is to perform it at a strategic instant when it can be made undetectably. In this way, there are no step changes in network dynamics experienced by the RLC network; hence, there is no time lost to transition recovery.

The instant to switch the inductors would be when the inductor current is zero. This occurs twice during a given cycle of the power carrier; hence, it becomes possible to transmit two bits of data per cycle. A nominal inductive link with a 1 MHZ power carrier frequency can support an in-link data transfer rate of 2 Mbps which has not been achieved in prior art systems.

To recover the power carrier signal, synchronous AM can be used. Band width limitations of the signal-receiving coil can be eliminated if the coil is not resonated. The voltage gain experienced through resonation is irrelevant in this circumstance due to the inherent strength of the transmitted signal.

A Class-D amplifier is best suited for this type of application, since it achieves much higher power conversion efficiency than the most efficient linear-type amplifiers (Class-C). One drawback, however, of a Class-D amplifier is that harmonic generation is prevalent. Fortunately, the band-pass filtering performed by the resonant energizer-output circuit removes most harmonic content, particularly at much higher frequencies, where it is potentially detrimental due to conflicts with telemeter transmissions.

Half-cycle amplitude modulation maintains the linear system behavior of the energizing resonant circuits (comprised of an energizing coil and associated resonating capacitor), while instantaneously modulating the amplitude of the emanating magnetic field. This is done by switching-out a section of the energizing coil, while substituting in its place an equivalent inductor that does not contribute magnetic field to the link. The substitution must be accomplished at zero crossings of the coil current when the inductor stored energy is zero.

Figure 9:
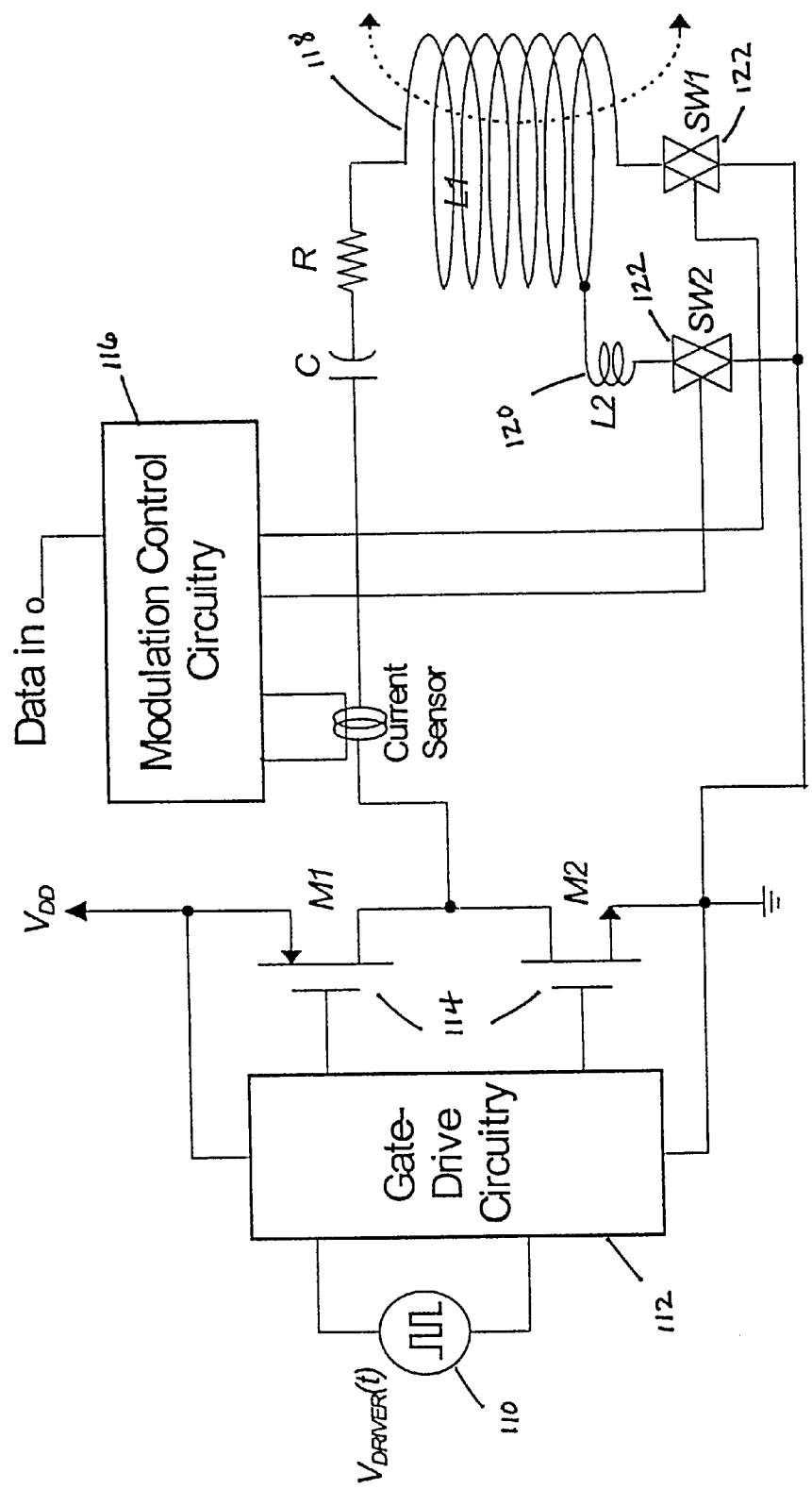
FIG. 9 illustrates a simplified schematic of an energizing coil having associated Half-Cycle Amplitude Modulation (HCAM) circuitry according to the present invention.

A simplified circuit schematic of the HCAM system is illustrated in FIG. 9. A square wave voltage signal 110 is fed through gate drive circuitry 112 and a pair of power MOSFETs 114. The output of the power MOSFETs is sensed and passed through modulation control circuitry 116 before driving a resonant RLC circuit where inductor 118 represents the energizing coil. A secondary coil 120 is connected to the energizing coil at a tap point such that the inductance of the secondary coil is equivalent to the tapped out portion of the energizing coil. A pair of bilateral switches 122 are included, one connected to the energizing coil 118 and the other connected to the secondary coil 120. The switches 122 are also connected to the modulation control circuitry 116.

Figure 10:
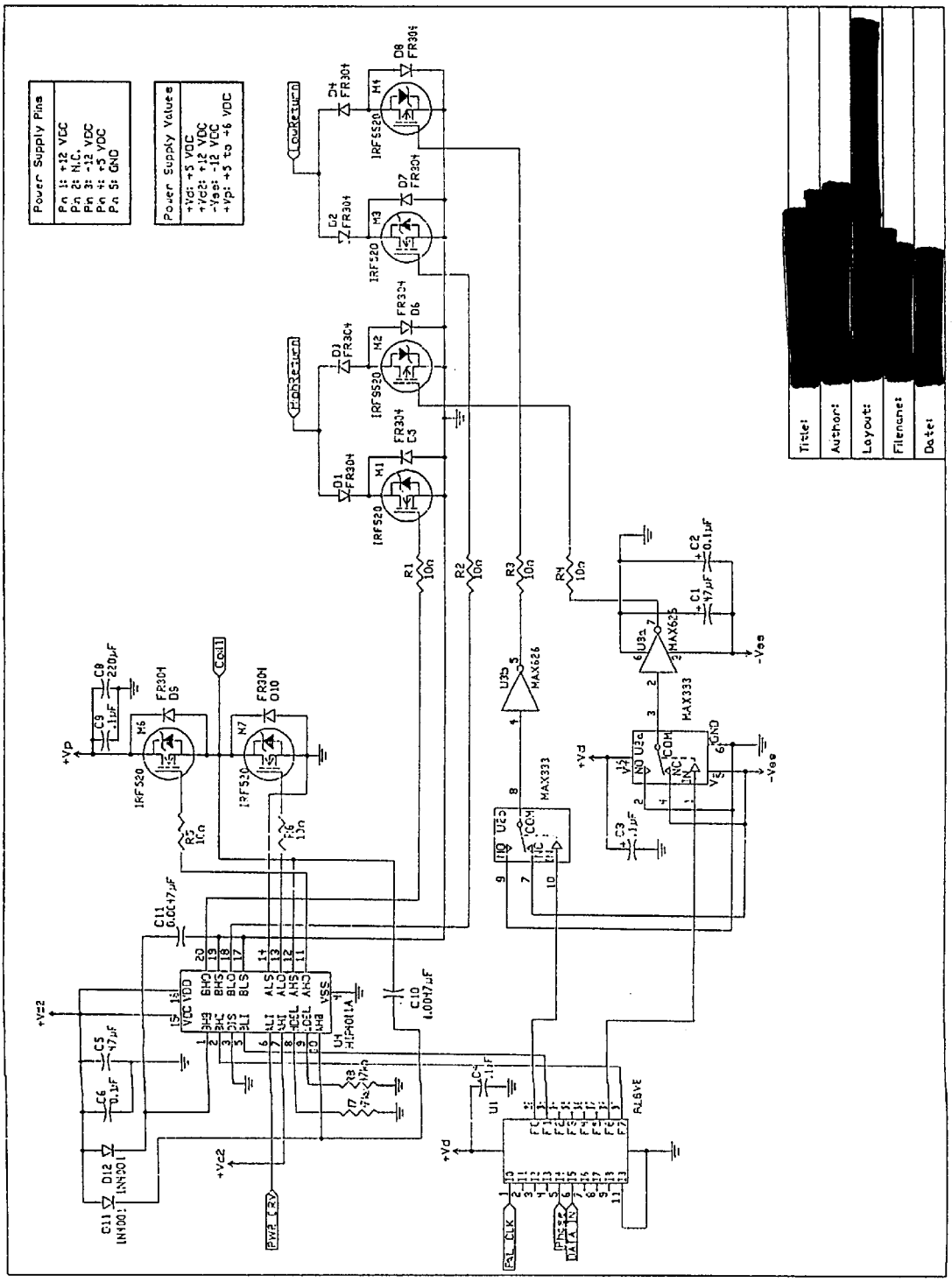
FIG. 10 illustrates a more detailed circuit schematic of the Half-Cycle Amplitude Modulation (HCAM) system according to the present invention.

A more detailed circuit schematic used to implement the HCAM concept is shown in FIG. 10. It comprises a switch controller (U1), MOSFET driver circuitry (U2–U4), and power MOSFETs (M1–M4) for coil driving and current steering. U4 is an H-bridge driver chip designed to drive 4 n-channel power MOSFETs. Two H-bridge channels are used to drive a half-bridge (M6 and M7) which in-turn generates the square-wave voltage waveform for the energizing circuit. A simple TTL-level clock signal is presented to pin 6 of U1 for driving the output at the desired frequency. Each of the implemented bilateral switches comprise an n-channel and p-channel MOSFET and four diodes. The complementary MOSFETs are needed so that current can pass in either direction through the switch. With respect to the left-most switch (indicated by the signal "HighReturn"), diodes D5 and D6 act to protect MOSFETs under severe reverse bias conditions. Diodes D1 and D3 block current from passing through the reverse direction, in the case when a MOSFET is turned off. The "LowReturn" switch operates in an identical manner.

N-channel MOSFETs in the bilateral switches are driven by the two remaining channels of U1. In order to drive the p-channel devices, level shifting must be achieved, as they are turned-on by negative voltages. The negative driving voltages are generated through a MOSFET driver chip (M3) that is referenced to –Vss, rather than ground. Level-shifted control signals are generated by the multiplexers of U2 that convert the TTL-level inputs down to –Vss (low) and 0 volts (high).

The driving signals are generated by the GAL U1. When presented with the phase polarity of the energizing current waveform, a data bit, and a clocking signal (derived from the energizing-current waveform), the programmed finite-state matching algorithm causes the bilateral switch MOSFETs accordingly. To avoid the need for exact switch timing, the MOSFETs are switched during the half-cycle before they will be used. For example, if a high-to-low transition is to be achieved in the radiated magnetic field, then sometime during the high, positive phase when M1 is active, M4 will be turned on. Thus current is steered automatically as the data transitions from high to low. Once current is flowing exclusively through M4, M1 can be turned off (unless it is needed for a "high" signal immediately following the current phase).

For the ideal case of a sinusoid alternating between two magnitudes ($A_1$ and $A_2$) every half cycle, one can obtain the frequency spectra according to the following:

$$S(j\omega) = \frac{A_2 - A_1}{\pi} + j\frac{A_1 + A_2}{4}[\delta(\omega + \omega_0) - \delta(\omega - \omega_0)] + \frac{A_1 - A_2}{\pi}\sum_{n=2,4,6}\frac{\delta(\omega + \omega_0) - \delta(\omega - \omega_0)}{n^2 - 1}$$

Figure 11:
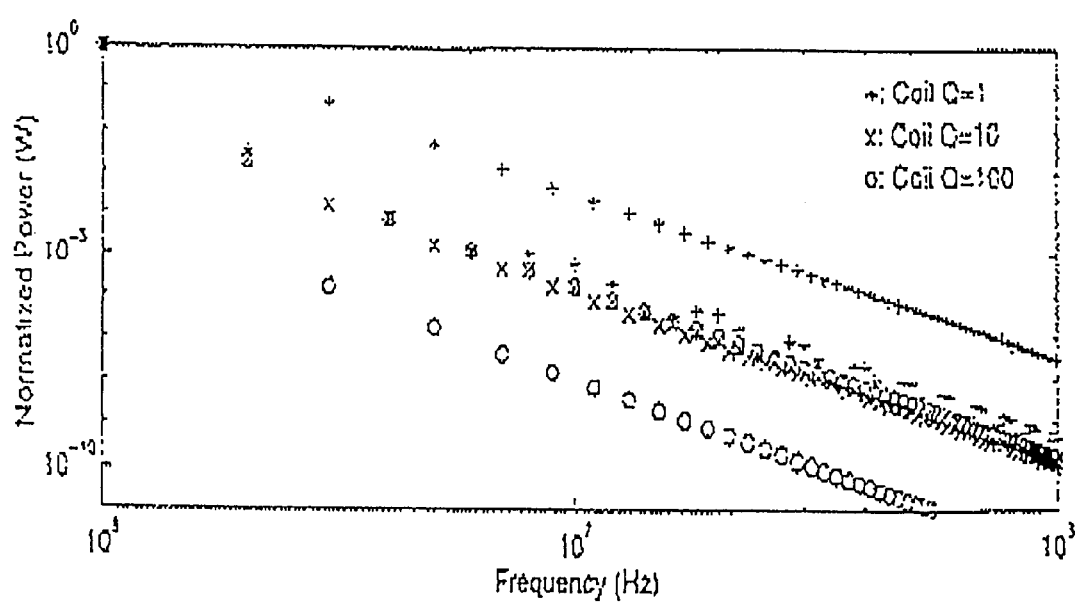
FIG. 11 illustrates a harmonic spectra graph of coil current for varying coil Qs according to the present invention.

The equation above is comprised of three parts: a DC term, a first harmonic term, and higher-order harmonics. One should note the fall-off in harmonic amplitude with respect to frequency is related to $1/(n^2-1)$. Therefore, harmonic power falls-off even more rapidly as the square of this quantity. Low-harmonic content of the power carrier signal at telemeter transmission frequencies is important since implant device transmissions could potentially go undetected due to the overpowering presence of power carrier harmonics. The higher the Q the more harmonic rejection of the square wave will occur as illustrated in the frequency spectra graphs of FIG. 11.

The foregoing descriptions of MVS and HCAM are complementary of one another and can be integrated into a single system such as those for biomedical applications. In cardiac mapping, for instance, Magnetic Vector Steering (MVS) can be used to provide power to and communicate with biomedical implants placed in regions of interest about the heart of a patient such as ischemic or infarcted areas. Half-Cycle Amplitude Modulation (HCAM) can then be used to communicate at higher bandwidth data rates with the biomedical implants powered under MVS.

The preferred embodiment of the present invention is intended for biomedical applications, such as, but not limited to, cardiac mapping. It is, however, suitable for any inductively powered application requiring remote powering of a device and/or data exchange with a remote device. As such, this applies to virtually any situation in which battery-less devices are to operate within a restricted environment.

In the claims, means-plus-function clauses, to the extent they are recited, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. An amplitude modulation method of transmitting data at up to two bits per cycle of a power carrier signal having two zero crossing points per cycle for use with inductively powered systems, said method comprising the steps of:

(a) detecting when the current through an energizing coil is zero;

(b) switching in or out a section of said energizing coil in order to modulate the magnetic field of said energizing coil at instants when the energizing coil current is zero; and (c) replacing said switched energizing coil section with an equivalent inductance.

2. A amplitude modulation method of transmitting data at up to two bits per cycle of a power carrier signal having two zero crossing points per cycle for use with inductively powered systems employing advanced switching to compensate for inherent timing delays to establish a desired circuit path at the instance of the zero crossing state, said method comprising the steps of:

(a) switching in or out, in the opposite phase, a section of an energizing coil in order to modulate the magnetic field of said energizing coil prior to a zero crossing point; and (b) replacing said switched energizing coil section with an equivalent inductance.

* * * * *